United States Patent
Hale et al.

(10) Patent No.: US 7,358,258 B2
(45) Date of Patent: Apr. 15, 2008

(54) PRODRUGS OF AN ERK PROTEIN KINASE INHIBITOR

(75) Inventors: Michael Robin Hale, Bedford, MA (US); Francois Maltais, Tewksbury, MA (US); Gabriel Martinez-Botella, West Roxbury, MA (US); Judith Straub, Santa Cruz, CA (US); Qing Tang, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/129,114

(22) Filed: May 13, 2005

(65) Prior Publication Data

US 2006/0058318 A1    Mar. 16, 2006

Related U.S. Application Data

(60) Provisional application No. 60/571,283, filed on May 14, 2004.

(51) Int. Cl.
| | |
|---|---|
| *C07D 403/04* | (2006.01) |
| *A61K 31/506* | (2006.01) |
| *A61P 35/00* | (2006.01) |
| *A61P 9/10* | (2006.01) |
| *A61P 11/06* | (2006.01) |
| *A61P 25/28* | (2006.01) |

(52) U.S. Cl. ...................................... 514/275; 544/331

(58) Field of Classification Search ................. 544/331, 544/275; 514/275
See application file for complete search history.

(56) References Cited

U.S. PATENT DOCUMENTS 5,776,954 A     7/1998  de Laszlo et al. .......... 514/340

FOREIGN PATENT DOCUMENTS

| WO | WO 02/064586 A2 | 8/2002 |
| WO | WO 03/091246 A1 | 11/2003 |
| WO | WO 2004/005283 A1 | 1/2004 |

OTHER PUBLICATIONS

Cecil Textbook of Medicine, edited by Bennet, J.C., and Plum F., 20th edition, vol. 1, 1004-1010, 1996.*
Duhe et al. Cell Biochem. Biophys. 34(1): 17-59, 2001.*
Rane et al., Oncogene 19(49): 5662-79, 2000.*
Kim et al., Curr. Opin Genet Dev. 10(5): 508-514, 2000.*
Mass, R. D., Int. J. Radiation Oncology Bio. Phys.vol. 58(3): 932-940, 2004.*
Fabbro et al. Pharmacology & therapeutics 93, 79-98, 2002.*

* cited by examiner

*Primary Examiner*—Venkataraman Balasubram
(74) *Attorney, Agent, or Firm*—Daniel A. Pearson

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

6 Claims, No Drawings

PRODRUGS OF AN ERK PROTEIN KINASE INHIBITOR

CROSS REFERENCE TO RELATED APPLICATIONS

This application claims priority to U.S. Provisional Patent Application 60/571,283 filed May 14, 2004, the entire contents of which are hereby incorporated herein by reference.

TECHNICAL FIELD OF INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J., 9:576-596 (1995); Knighton et al., Science, 253:407-414 (1991); Hiles et al., Cell, 70:419-429 (1992); Kunz et al., Cell, 73:585-596 (1993); Garcia-Bustos et al., EMBO J., 13:2352-2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

ERK2 is a widely distributed protein kinase that achieves maximum activity when both Thr183 and Tyr185 are phosphorylated by the upstream MAP kinase kinase, MEK1 (Anderson et al., 1990, Nature 343, 651; Crews et al., 1992, Science 258, 478). Upon activation, ERK2 phosphorylates many regulatory proteins, including the protein kinases Rsk90 (Bjorbaek et al., 1995, J. Biol. Chem. 270, 18848) and MAPKAP2 (Rouse et al., 1994, Cell 78, 1027), and transcription factors such as ATF2 (Raingeaud et al., 1996, Mol. Cell Biol. 16, 1247), Elk-1 (Raingeaud et al. 1996), c-Fos (Chen et al., 1993 Proc. Natl. Acad. Sci. USA 90, 10952), and c-Myc (Oliver et al., 1995, Proc. Soc. Exp. Biol. Med. 210, 162). ERK2 is also a downstream target of the Ras/Raf dependent pathways (Moodie et al., 1993, Science 260, 1658) and relays the signals from these potentially oncogenic proteins. ERK2 has been shown to play a role in the negative growth control of breast cancer cells (Frey and Mulder, 1997, Cancer Res. 57, 628) and hyperexpression of ERK2 in human breast cancer has been reported (Sivaraman et al., 1997, J. Clin. Invest. 99, 1478). Activated ERK2 has also been implicated in the proliferation of endothelin-stimulated airway smooth muscle cells, suggesting a role for this kinase in asthma (Whelchel et al., 1997, Am. J. Respir. Cell Mol. Biol. 16, 589).

Overexpression of receptor tyrosine kinases such as EGFR and ErbB2 (Arteaga C L, 2002, Semin Oncol. 29, 3-9; Eccles S A, 2001, J Mammary Gland Biol Neoplasia 6:393-406; Mendelsohn J & Baselga J, 2000, Oncogene 19, 6550-65), as well as activating mutations in the Ras GTPase proteins (Nottage M & Siu L L, 2002, Curr Pharm Des 8, 2231-42; Adjei A A, 2001, J Natl Cancer Inst 93, 1062-74) or B-Raf mutants (Davies H. et al., 2002, Nature 417, 949-54; Brose et al., 2002, Cancer Res 62, 6997-7000) are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that has been associated with the control of proliferation, differentiation, anchorage-independent cell survival, and angiogenesis, contributing to a number of processes that are important for the formation and progression of malignant tumors. These data suggest that an ERK1/2 inhibitor will exert pleiotropic activity, including proapoptotic, anti-proliferative, anti-metastatic and anti-angiogenic effects, and offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates (ref). Ras mutations have also been identified in 9-15% of melanomas, but B-Raf somatic missense mutations conferring constitutive activation are more frequent and found in 60-66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and has been associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as promising therapeutic target for the treatment of melanoma, a currently untreatable disease.

Accordingly, there is a great need to develop compounds useful as inhibitors of protein kinases. In particular, it would be desirable to develop compounds that are useful as inhibitors of ERK protein kinase particularly given the inadequate treatments currently available for the majority of the disorders implicated in its activation.

SUMMARY OF THE INVENTION

It has now been found that compounds of this invention, and pharmaceutically acceptable compositions thereof, are effective prodrugs of an inhibitor of ERK protein kinase. These compounds have the general formula I:

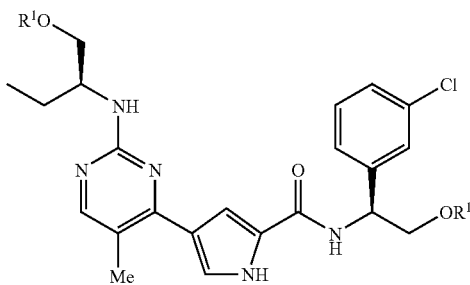

or a pharmaceutically acceptable salt thereof, wherein $R^1$ is as defined below.

These compounds, and pharmaceutically acceptable compositions thereof, are useful for treating or lessening the severity of a variety of disorders, especially proliferative disorders such as cancer. The prodrugs described herein impart improved physical and/or pharmacokinetic properties of the parent compound.

The compounds provided by this invention are also useful for the study of kinases in biological and pathological phenomena and the study of intracellular signal transduction pathways mediated by such kinases, and the comparative evaluation of new kinase inhibitors.

DETAILED DESCRIPTION OF CERTAIN EMBODIMENTS OF THE INVENTION

1. General Description of Compounds of the Invention:
The present invention relates to a compound of formula I:

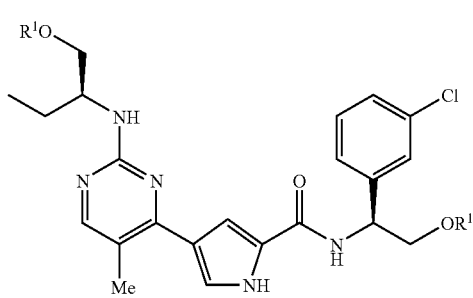

or a pharmaceutically acceptable salt thereof, wherein:
each $R^1$ is independently hydrogen, $T-C(O)R^2$, $T-C(O)OR^2$, $T-C(O)-Q-R^2$, $T-C(O)-(CH_2)_n-C(O)OR^2$, $T-C(O)-(CH_2)_n-C(O)N(R^3)_2$, $T-C(O)-(CH_2)_n-CH(R^2)N(R^3)_2$, $T-P(O)(OR^2)_2$, provided that at least one $R^1$ is not hydrogen;
each T is independently a valence bond or $-C(R)_2O-$;
each $R^2$ is independently hydrogen, an optionally substituted $C_{1-6}$ aliphatic group or an optionally substituted 5-8 membered saturated, partially unsaturated, or fully unsaturated ring having 0-4 heteroatoms independently selected from nitrogen, oxygen, or sulfur;
each $R^3$ is independently hydrogen, $C(O)R^2$, $C(O)OR^2$, $S(O)_2R^2$, $OR^2$, an optionally substituted $C_{1-6}$ aliphatic group or an optionally substituted 5-8 membered saturated, partially unsaturated, or fully unsaturated ring having 0-4 heteroatoms independently selected from nitrogen, oxygen, or sulfur, or:
two $R^3$ on the same nitrogen atom taken together with the nitrogen atom bound thereto form a 4-7 membered saturated, partially unsaturated, or fully unsaturated ring having 1-3 heteroatoms in addition to the nitrogen atom, independently selected from nitrogen, oxygen, or sulfur;
each n is 0-6;
Q is an optionally substituted $C_{1-10}$ alkylidene chain wherein zero to four methylene units of Q are independently replaced by $-O-$, $-N(R)-$, $-S-$, $-S(O)-$, $-S(O)_2-$, or $-C(O)-$; and
R is hydrogen or an optionally substituted $C_{1-6}$ aliphatic.

2. Compounds and Definitions:
Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "prodrug" refers to a derivative of a parent drug molecule that requires transformation within the body in order to release the active drug, and that has improved physical and/or delivery properties over the parent drug molecule. Prodrugs are designed to enhance pharmaceutically and/or pharmacokinetically based properties associated with the parent drug molecule. The advantage of a prodrug lies in its physical properties, such as enhanced water solubility for parenteral administration at physiological pH compared to the parent drug, or it enhances absorption from the digestive tract, or it may enhance drug stability for long-term storage. In recent years several types of bioreversible derivatives have been exploited for utilization in designing prodrugs. Using esters as a prodrug type for drugs containing carboxyl or hydroxyl function is known in the art as described, for example, in "The Organic Chemistry of Drug Design and Drug Interaction" Richard Silverman, published by Academic Press (1992).

As used herein, the term "parent compound" refers to the compound of formula I wherein both R$^1$ groups are simultaneously hydrogen.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; R°; OR°; SR°; 1,2-methylene-dioxy; 1,2-ethylene-dioxy; phenyl (Ph) optionally substituted with R°; —O(Ph) optionally substituted with R°; (CH$_2$)$_{1-2}$(Ph), optionally substituted with R°; CH═CH(Ph), optionally substituted with R°; NO$_2$; CN; N(R°)$_2$; NR°C(O)R°; NR°C(O)N(R°)$_2$; NR°CO$_2$R°; —NR°NR°C(O)R°; NR°NR°C(O)N(R°)$_2$; NR°NR°CO$_2$R°; C(O)C(O)R°; C(O)CH$_2$C(O)R°; CO$_2$R°; C(O)R°; C(O)N(R°)$_2$; OC(O)N(R°)$_2$; S(O)$_2$R°; SO$_2$N(R°)$_2$; S(O)R°; NR°SO$_2$N(R°)$_2$; NR°SO$_2$R°; C(═S)N(R°)$_2$; C(═NH)—N(R°)$_2$; or (CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, O(Ph), or CH$_2$(Ph), or, notwithstanding the definition above, two independent occurrences of R°, on the same substituent or different substituents, taken together with the atom(s) to which each R° group is bound, form a 3-8 membered cycloalkyl, heterocyclyl, aryl, or heteroaryl ring having 0-3 heteroatoms independently selected from nitrogen, oxygen, or sulfur. Optional substituents on the aliphatic group of R° are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}\ aliphatic)$, or $haloC_{1-4}aliphatic$, wherein each of the foregoing $C_{1-4}aliphatic$ groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =N*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from R$^+$, N(R$^+$)$_2$, C(O)R$^+$, CO$_2$R$^+$, C(O)C(O)R$^+$, C(O)CH$_2$C(O)R$^+$, SO$_2$R$^+$, SO$_2$N(R$^+$)$_2$, C(=S)N(R$^+$)$_2$, C(=NH)—N(R$^+$)$_2$, or NR$^+$SO$_2$R$^+$; wherein R$^+$ is hydrogen, an optionally substituted $C_{1-6}$ aliphatic, optionally substituted phenyl, optionally substituted O(Ph), optionally substituted CH$_2$(Ph), optionally substituted (CH$_2$)$_{1-2}$(Ph); optionally substituted CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R$^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

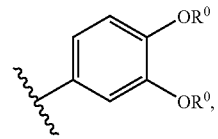

these two occurrences of R° are taken together with the oxygen atoms to which they are bound to form a fused 6-membered oxygen containing ring:

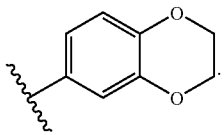

It will be appreciated that a variety of other rings can be formed when two independent occurrences of R°(or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

According to certain embodiments, the R$^1$ moiety of formula I is C(O)R$^2$. According to other embodiments, the R$^1$ moiety of formula I is C(O)R$^2$ wherein R$^2$ is an optionally substituted $C_{1-6}$ aliphatic group. Examples of such R$^2$ groups include methyl, CH$_2$phenyl ("benzyl"), ethyl, isopropyl, t-butyl, and the like. Another aspect of the present invention relates to a compound of formula I wherein R$^1$ is C(O)R$^2$ and R$^2$ is an optionally substituted 5-8 membered saturated, partially unsaturated, or fully unsaturated ring having 0-4 heteroatoms independently selected from nitrogen, oxygen, or sulfur. Such R$^2$ groups include 5-6 membered heterocyclic rings having 1-2 heteroatoms independently selected from nitrogen, oxygen, or sulfur. Examples of such R$^2$ groups include pyrrolidine, morpholine, thiomorpholine, piperidine, and the like.

According to other embodiments, the R$^1$ moiety of formula I is C(O)OR$^2$. In still other embodiments, the R$^1$ moiety of formula I is C(O)OR² wherein R² is an optionally substituted C₁₋₆ aliphatic group. Examples of such R² groups include methyl, benzyl, ethyl, isopropyl, t-butyl, and the like. Another aspect of the present invention relates to a compound of formula I wherein R¹ is C(O)OR² and R² is an optionally substituted 5-8 membered saturated, partially unsaturated, or fully unsaturated ring having 0-4 heteroatoms independently selected from nitrogen, oxygen, or sulfur. Such R² groups include optionally substituted phenyl, or a 5-6 membered heterocyclic ring having 1-2 heteroatoms independently selected from nitrogen, oxygen, or sulfur. Examples of such R² groups include pyrrolidine, morpholine, thiomorpholine, piperidine, and the like.

According to other embodiments, the R¹ moiety of formula I is C(O)-Q-R². Still other embodiments related to a compound of formula I wherein R¹ is C(O)-Q-R² and Q is an optionally substituted C₁₋₈ alkylidene chain wherein zero to four methylene units of Q are independently replaced by —O—, —N(R)—, —S—, —S(O)—, —S(O)₂—, or —C(O)— and R² is as defined in general and in classes and subclasses described above and herein. According to another embodiment, Q is an optionally substituted C₁₋₈ alkylidene chain wherein two to four methylene units of Q are independently replaced by —O—. Such Q groups include —CH₂OCH₂CH₂O—, —CH₂OCH₂CH₂OCH₂CH₂O—, and the like.

Yet another aspect of the present invention provides a compound of formula I wherein R¹ is C(O)—(CH₂)ₙ—CH(R²)N(R³)₂. In certain embodiments, n is 0-2. In other embodiments, R² is an optionally substituted C₁₋₆ aliphatic group. Examples of such R² groups include methyl, benzyl, ethyl, isopropyl, cyclopropyl, t-butyl, and the like. The R³ groups of the C(O)—(CH₂)ₙ—CH(R²)N(R³)₂ of formula I include hydrogen and an optionally substituted C₁₋₆ aliphatic group. Examples of such groups include methyl, benzyl, ethyl, isopropyl, t-butyl, and the like.

In certain embodiments, the C(O)—(CH₂)ₙ—CH(R²)N(R³)₂ moiety of formula I provides an amino acid ester. Such amino acid esters include valine ester, leucine ester, isoleucine ester, alpha-t-butylglycine ester, dimethyl glycine ester, and the like.

Another aspect contemplated by the present invention relates to a compound of formula I wherein the C(O)—(CH₂)ₙ—CH(R²)N(R³)₂ moiety provides an N-alkylated amino acid ester, especially an N-methylated amino acid ester wherein the amino acid ester includes those described above and herein.

In certain embodiments of the present invention, the R¹ group of formula I is P(O)(OR²)₂. In other embodiments, each R² of the P(O)(OR²)₂ group is independently hydrogen or an optionally substituted C₁₋₆ aliphatic group. Examples of such R² groups include methyl, benzyl, ethyl, isopropyl, t-butyl, and the like. In still other embodiments, the R¹ group of formula I is P(O)(OH)₂.

In certain embodiments, the R¹ group of formula I is C(O)R², C(O)—(CH₂)ₙ—CH(R²)N(R³)₂, C(O)-Q-R², or P(O)(OH)₂.

In other embodiments, the R¹ group of formula I is C(O)OR² or P(O)(OR²)₂

According to one aspect of the present invention, a compound of formula I is provided wherein T is a valence bond and each R¹ group is as defined generally and in classes and subclasses described above and herein.

According to another aspect of the present invention, a compound of formula I is provided wherein T is —C(R)₂O— and each R¹ group is as defined generally and in classes and subclasses described above and herein. In certain embodiments, each R moiety of —C(R)₂O— is hydrogen such that T is —CH₂O—. In other embodiments, each R moiety of —C(R)₂O— is independently hydrogen, methyl, ethyl, or propyl.

Representative compounds of formula I are set forth in Table 1 below.

TABLE 1

Examples of Compounds of Formula I:

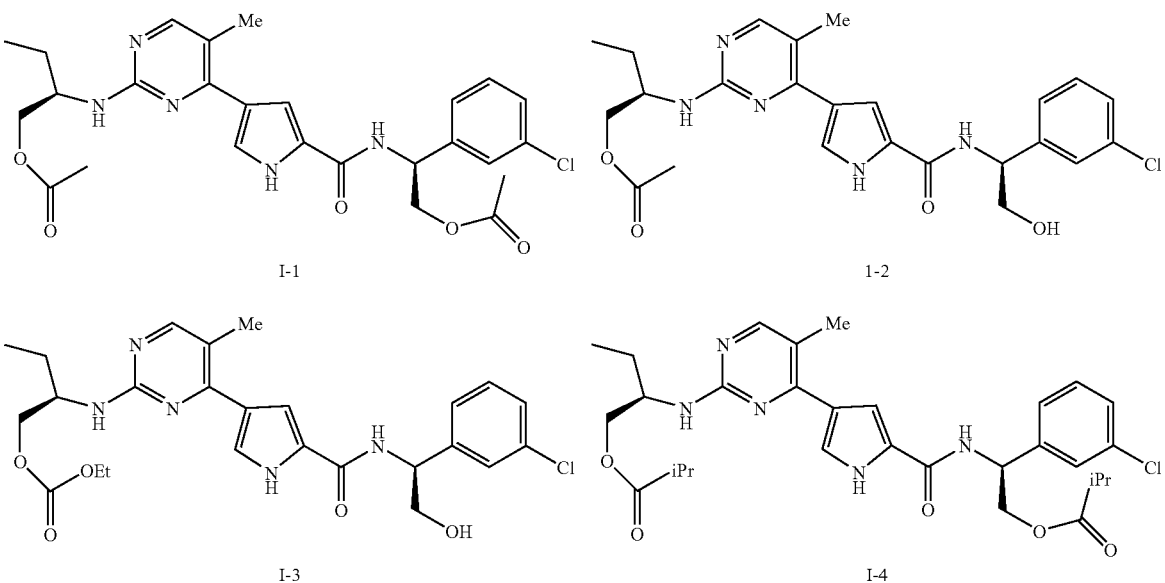

I-1

I-2

I-3

I-4

TABLE 1-continued
Examples of Compounds of Formula I:
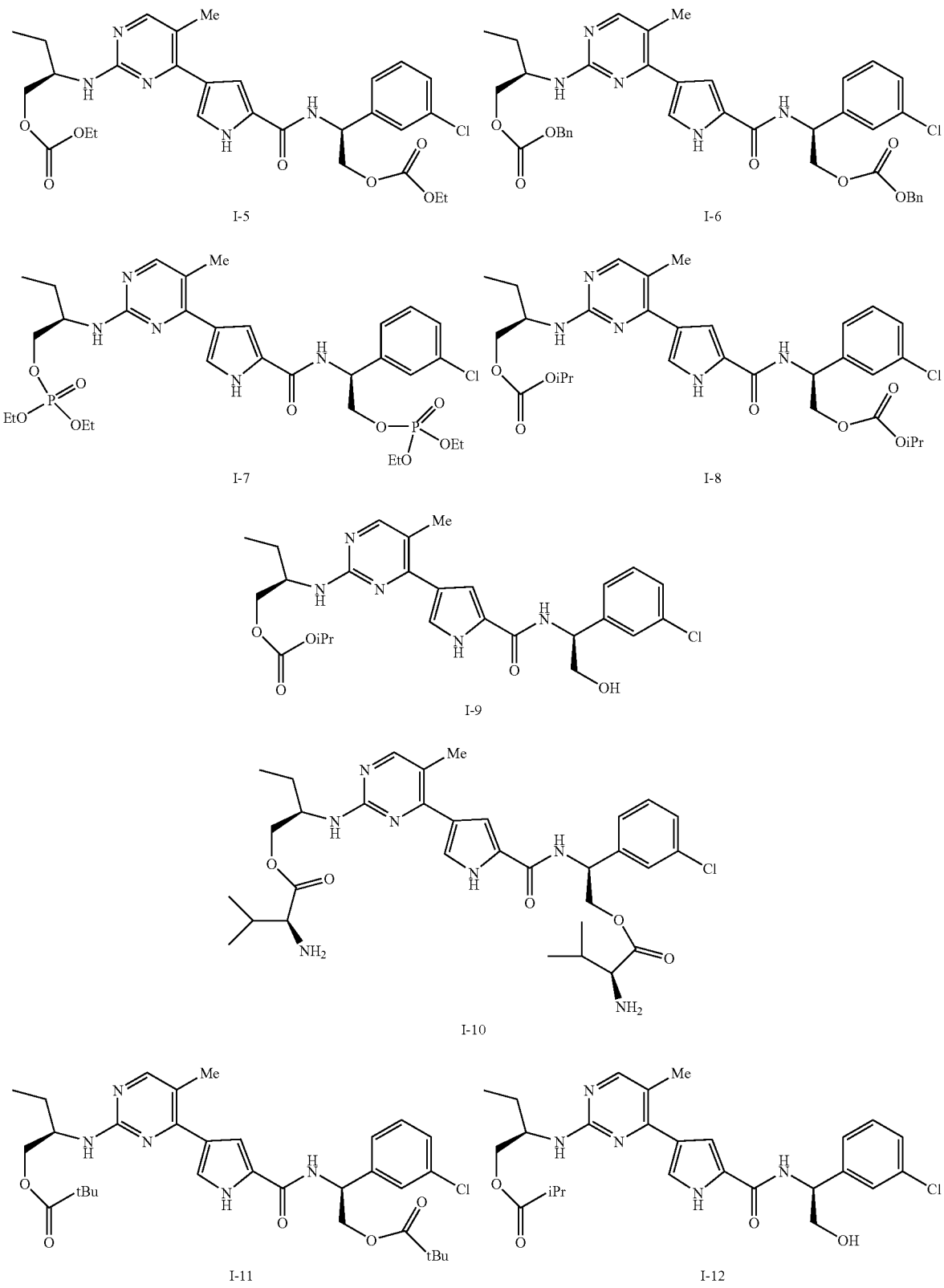

TABLE 1-continued
Examples of Compounds of Formula I:
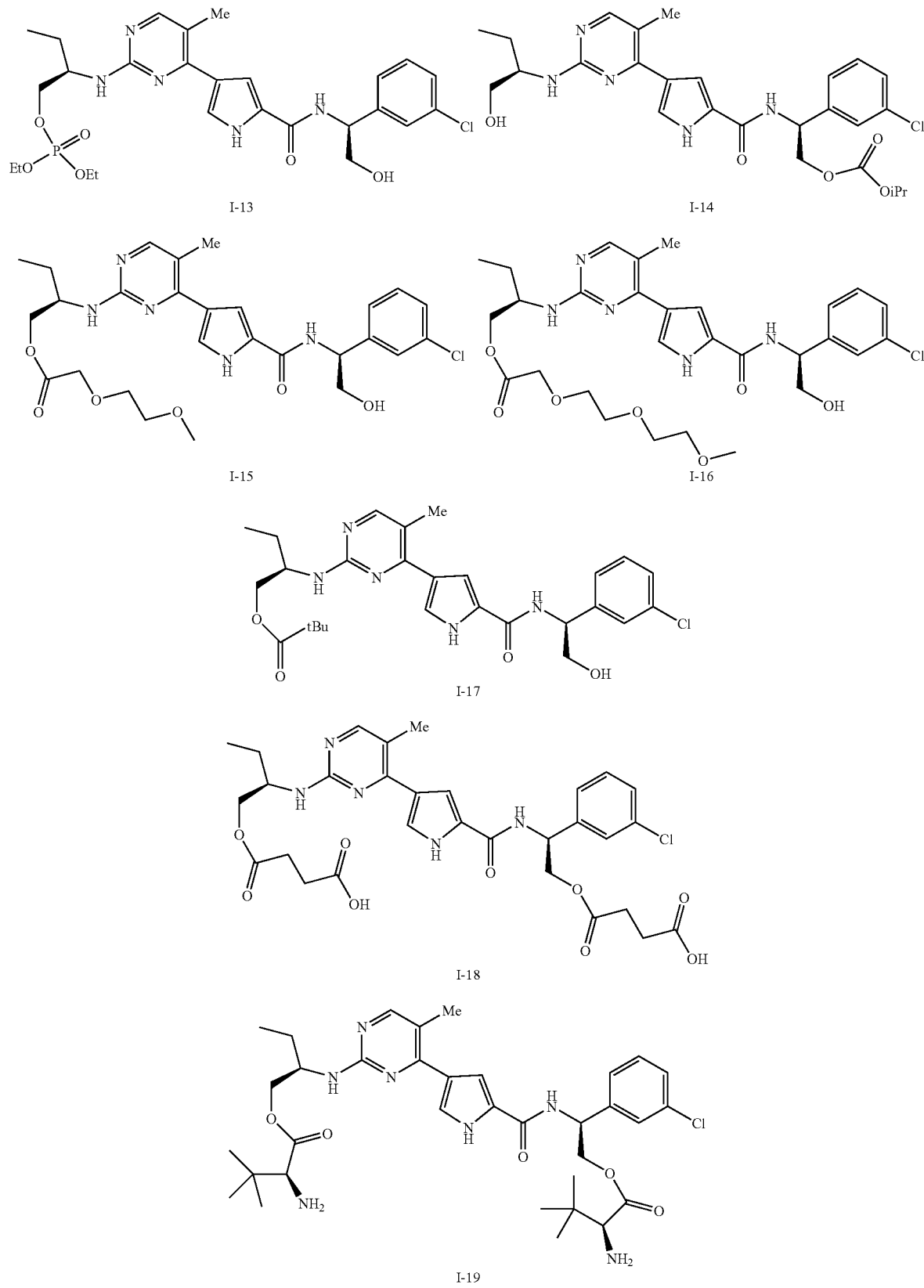

TABLE 1-continued
Examples of Compounds of Formula I:
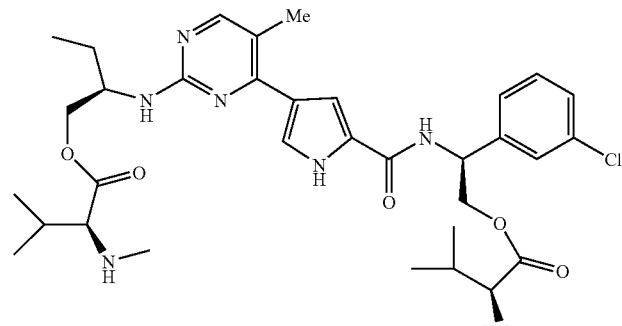
I-20
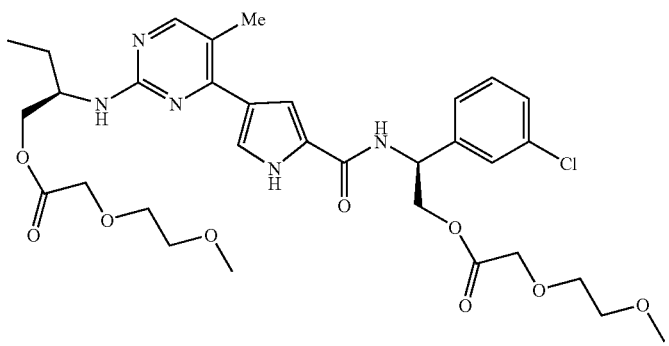
I-21
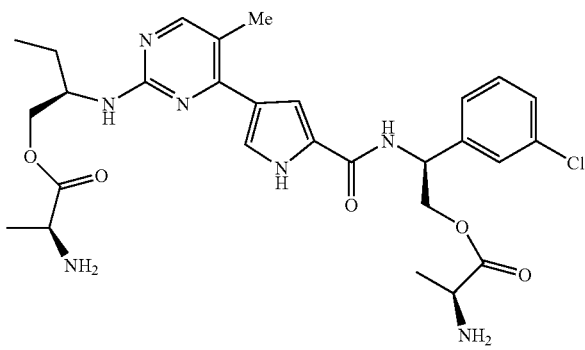
I-22
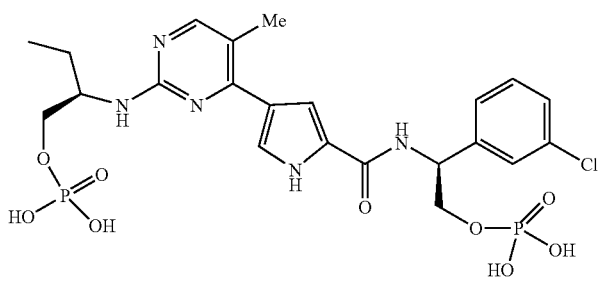
I-23

TABLE 1-continued
Examples of Compounds of Formula I:
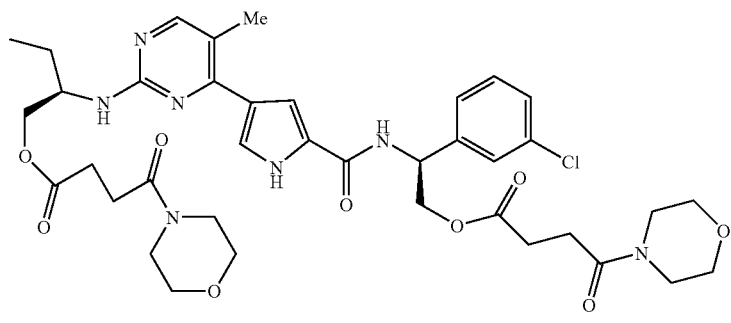
I-24
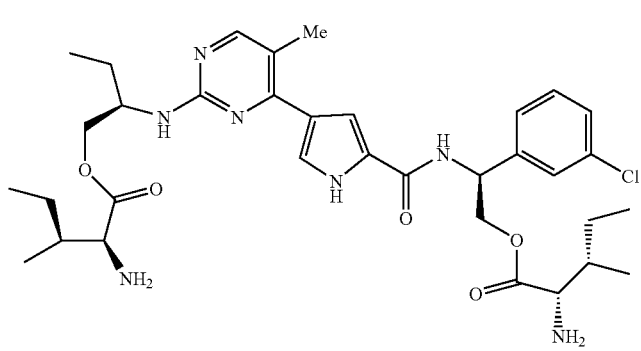
I-25
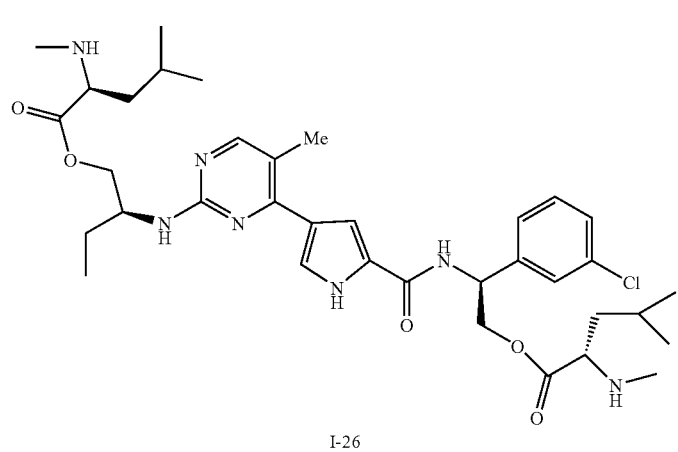
I-26
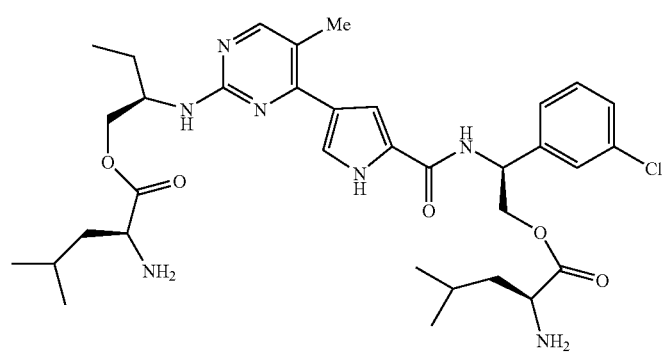
I-27

TABLE 1-continued
Examples of Compounds of Formula I:
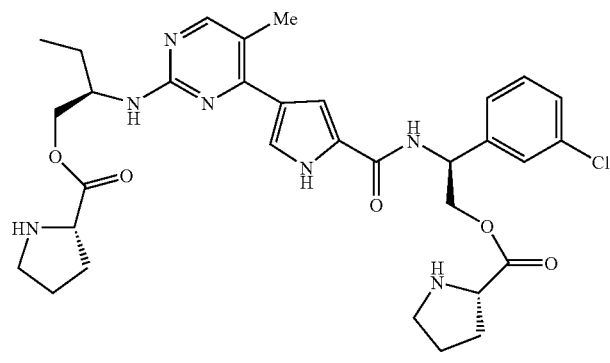
I-28
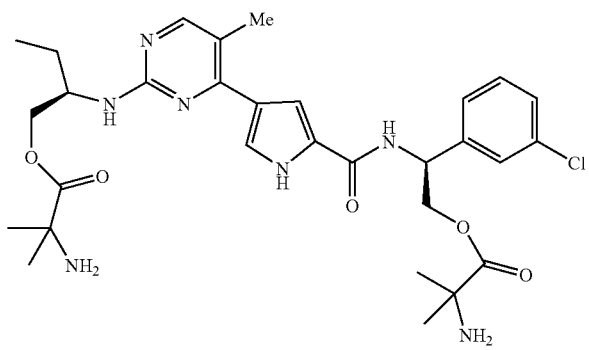
I-29
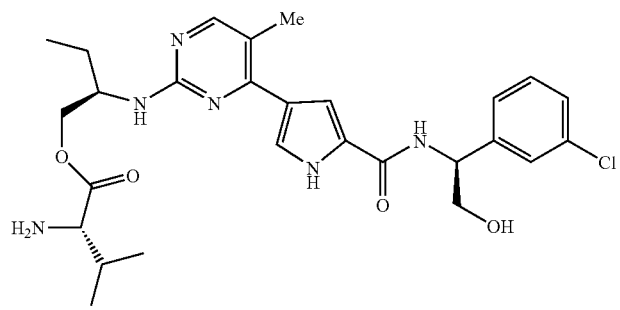
I-30
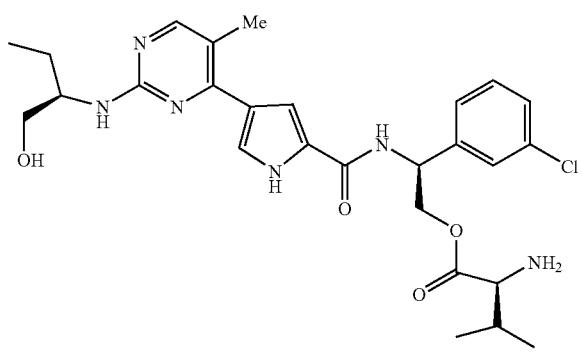
I-31

TABLE 1-continued
Examples of Compounds of Formula I:
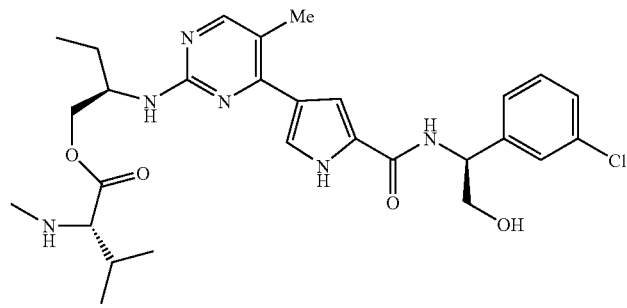
I-32
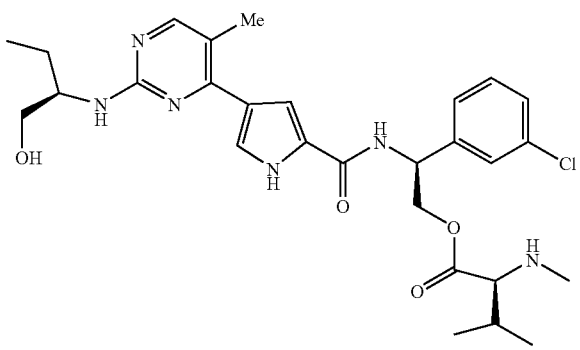
I-33
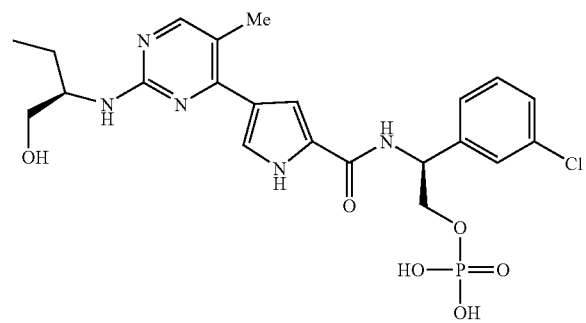
I-34
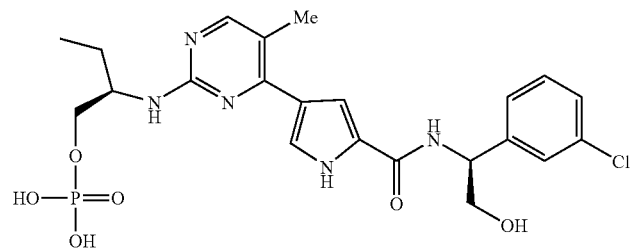
I-35
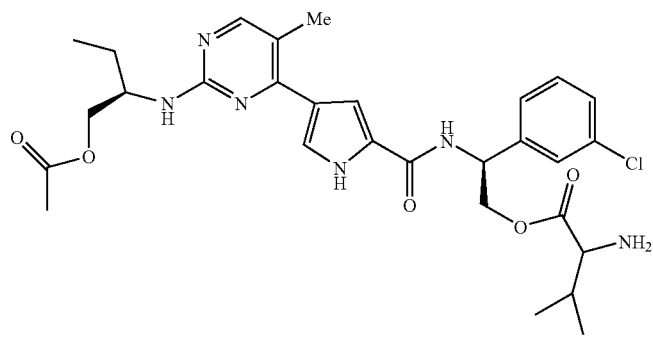
I-36

TABLE 1-continued

Examples of Compounds of Formula I:

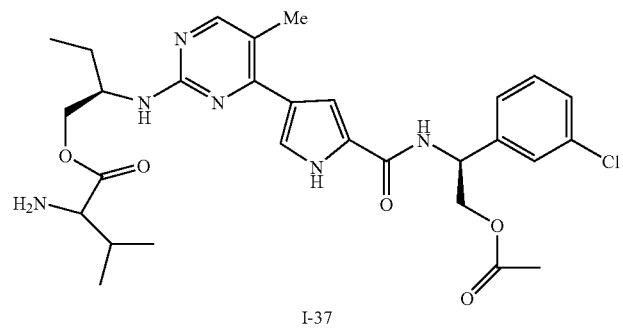

I-37

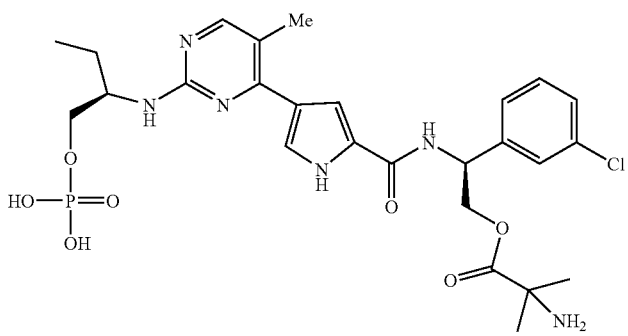

I-38

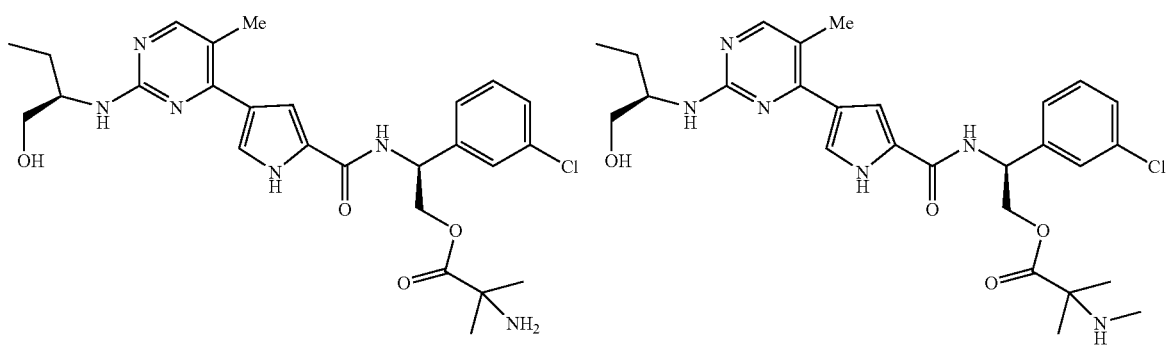

I-39  I-40

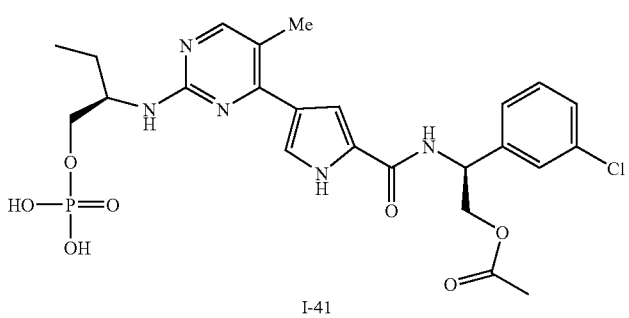

I-41

4. General Methods of Providing the Present Compounds:

The parent compound of the present invention may be prepared according to methods known to one or ordinary skill in the art and by those described in WO 02/064586, the disclosure of which is hereby incorporated by reference.

The compounds of this invention may be prepared or isolated in general by synthetic and/or pseudo-synthetic methods known to those skilled in the art for analogous compounds and as illustrated by the general schemes and the preparative examples that follow.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to cancer, autoimmune disorders, neurodegenerative and neurological disorders, schizophrenia, bone-related disorders, liver disease, and cardiac disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of ERK1 or ERK2 protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, an autoimmune disorder, a neurodegenerative or neurological disorder, liver disease, or a cardiac disorder is provided comprising administering an effective amount of a compound of the present invention, or a pharmaceutically acceptable composition comprising a compound of the present invention to a subject in need thereof. In certain embodiments of the present invention an "effective amount" of the compound or pharmaceutically acceptable composition is that amount effective for treating or lessening the severity of a disease, condition, or disorder selected from cancer, an autoimmune disorder, a neurodegenerative or neurological disorder, schizophrenia, a bone-related disorder, liver disease, or a cardiac disorder. The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of ERK protein kinases. In one embodiment, the compounds and compositions of the invention are inhibitors of one or both of ERK1 and ERK2 protein kinases and thus, without wishing to be bound by any particular theory, the compounds and compositions are particularly useful for treating or lessening the severity of a disease, condition, or disorder where activation of one or both of ERK1 and ERK2 protein kinases is implicated in the disease, condition, or disorder. When activation of ERK1 and/or ERK2 protein kinases is implicated in a particular disease, condition, or disorder, the disease, condition, or disorder may also be referred to as "ERK1- or ERK2-mediated disease", condition, or disease symptom. Accordingly, in another aspect, the present invention provides a method for treating or lessening the severity of a disease, condition, or disorder where activation of one or both of ERK1 and ERK2 protein kinases is implicated in said disease, condition, or disorder.

The activity of a compound utilized in this invention as an inhibitor of ERK1 and/or ERK2 protein kinases may be assayed in vitro, in vivo or in a cell line. In vitro assays include assays that determine inhibition of either the phosphorylation activity or ATPase activity of activated ERK1 or ERK2 protein kinases. Alternate in vitro assays quantitate the ability of the inhibitor to bind to ERK1 or ERK2 protein kinases. Inhibitor binding may be measured by radiolabelling the inhibitor prior to binding, isolating the inhibitor/ERK1 or inhibitor/ERK2 complex and determining the amount of radiolabel bound. Alternatively, inhibitor binding may be determined by running a competition experiment where new inhibitors are incubated with ERK1 or ERK2 protein kinases bound to known radioligands.

The term "measurably inhibit", as used herein means a measurable change in ERK1 or ERK2 protein kinase activity between a sample comprising said composition and a ERK1 or ERK2 protein kinase and an equivalent sample comprising ERK1 or ERK2 protein kinase in the absence of said composition. Such measurements of protein kinase activity are known to one of ordinary skill in the art and include those methods set forth herein below.

According to another embodiment, the invention relates to a method of inhibiting ERK1 or ERK2 protein kinase activity in a patient comprising the step of administering to said patient a compound of the present invention, or a composition comprising said compound.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting ERK1 or ERK2 protein kinase activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK1 or ERK2 protein kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, the term "$R_t$" refers to the HPLC retention time, in minutes, associated with the compound. Unless otherwise indicated, the HPLC method utilized to obtain the reported retention time is as follows:

Column: ODS-AQ 55 120A, 3.0×150 mm

Gradient: water:MeCN, 0.1% TFA (90:10→0:100) over 8 minutes

Flow: 1.0 mL/minute

Detection: 214 nm

Unless otherwise indicated, each $^1$H NMR was obtained at 500 MHz in $CDCl_3$ and compound numbers correspond to those compound numbers recited in Table 1.

The prodrugs of the present invention are prepared by derivatizing the hydroxyl moieties of the parent compound by a variety of methods known to one of ordinary skill in the art. These methods include, but are not limited to, acylation by a desired carboxylic acid (or activated derivative thereof) or phosphate formation. When the hydroxyl moiety of the parent compound is acylated by a desired amino acid, the amine moiety of the amino acid may be optionally protected by a suitable amino protecting group. Amino protecting groups are well known in the art and are described in detail in *Protecting Groups in Organic Synthesis*, Theodora W. Greene and Peter G. M. Wuts, 1991, published by John Wiley and Sons, the entirety of which is hereby incorporated by reference. Certain non-limiting examples describing the preparation of compounds of the present invention are set forth below.

Example 1

3-Methyl-2-methylamino-butyric acid 2-(4-{5-[1-(3-chloro-phenyl)-2-(3-methyl-2-methylamino-butyryloxy)-ethylcarbamoyl]-1H-pyrrol-3-yl}-5-methyl-pyrimidin-2-ylamino)-butyl ester, tris HCl salt t-Butoxycarbonyl-N-methyl valine (Advanced Chemtech, 15.6 g, 3 equivalents) was combined with 3-ethyl(3-dimethylaminopropyl) carbodiimide hydrochloride (Chem-Impex, 12.95 g, 3 equivalents), 1-hydroxybenzotriazole hydrate (Aldrich, 0.91 g, 0.3 equivalents) and 4-dimethylaminopyridine (8.26 g, 3 equivalents) in methylene chloride (100 mL) and stirred until homogeneous, about 15 minutes. The parent compound, 4-[2-(1-hydroxymethyl-propylamino)-5-methyl-pyrimidin-4-yl]-1H-pyrrole-2-carboxylic acid [1-(3-chloro-phenyl)-2-hydroxy-ethyl]-amide (10 g, 0.0225 mol, 1 equivalent) was added as a solution in DMF (20 mL) and the reaction was followed by HPLC. After 2 hours, the mixture was diluted with ethyl acetate, washed with 0.3N HCl, brine and saturated sodium bicarbonate, dried ($MgSO_4$) filtered and concentrated in vacuo. Purification by Combiflash (2 batches×120 g silica, hexanes/ethyl acetate gradient) afforded the Boc-protected compound as a pale yellow foam (14.9 g) $R_t$=8.90 min; MS FIA 870.0 (M+1) Boc-deprotection of the prodrug was achieved by dissolving the sample in methanol and adding 2.0N HCl in diethyl ether (Aldrich). After one hour, deprotection was complete and volatiles were removed in vacuo yielding the tris-hydrochloric acid salt of I-20 as a yellow solid (9.8 g). $R_t$=4.3 min, LCMS 670.1 (M+1) Calc: ($C_{34}H_{51}Cl_4N_7O_5$) C: 52.38; H: 6.59; N: 12.58; Cl: 18.19 Found: C: 52.25; H 6.90; N; 12.81; Cl: 18.10.

Example 2

3-Methyl-2-methylamino-butyric acid 2-(4-{5-[1-(3-chloro-phenyl)-2-(3-methyl-2-methylamino-butyryloxy)-ethylcarbamoyl]-1H-pyrrol-3-yl}-5-methyl-pyrimidin-2-ylamino)-butyl ester (I-20)

The HCl salt shown above (1.2 g) was dissolved in MeOH (5 mL) and ethyl acetate (100 mL) and washed with saturated sodium bicarbonate (×2) and brine then dried ($MgSO_4$) filtered and concentrated in vacuo to a yellow foam (1.0 g). LC/MS 670.1 (M+1); $^1$H NMR as recited in Table 2 below.

Example 3

Succinic acid, mono-[2-(4-{5-[2-(3-carboxy-propionyloxy)-1-(3-chloro-(S)-phenyl)-ethylcarbamyl]-1H-pyrrol-3-yl}-5-methyl-pyrimidin-2-ylamino)-(S)-butyl]ester (I-18)

In a flask containing 4-[2-(1-hydroxymethyl-(S)-propylamino)-5-methyl-pyrimidin-4-yl]-1H-pyrrole-2-carboxylic acid [1-(3-chloro-(S)-phenyl)-2-hydroxy-ethyl]-amide (2.15 g, 4.85 mmol) in 50 mL of dry pyridine was added a catalytic amount of DMAP and of succinic anhydride (1.2 g, 12.1 mmol, 2.5 equivalents). The mixture was heated at 80° C. for 24 hours and the reaction mixture concentrated in vacuo. The crude material was purified by preparative HPLC to afford the title compound (1.5 dg). HPLC, $R_t$=4.9 min. The bis sodium salt was made by treating the title compound (50.8 mg, 78.9 μmol) with a quantitative amount of sodium bicarbonate (2.0 equivalents, 1.58 mL of a 0.1 M solution) in methanol. After 10 minutes of stirring, the solvent was evaporated and the rest of the water was removed by lyophilization to afford the bis sodium salt as a white solid (49.3 mg). HPLC, $R_t$=4.9 min and $^1$H NMR (MeOH-d$_4$): 8.0 (s, 1H), 7.9 (s, 1H), 7.8 (s, 1H), 7.25-7.5 (m, 4H), 5.4 (m, 1H), 4.5 (m, 2H), 4.3-4.4 (m, 2H), 4.25 (m, 1H), 2.5-2.6 (s, m, 11H), 1.6-1.8 (m, 2H), 1.05 (t, 3).

Example 4

2-(S)-Amino-3-methyl-(S)-pentanoic acid 2-(4-{5-[2-(2-(S)-amino-3-methyl-(S)-pentanoyloxy)-1-(3-chloro-(S)-phenyl)-ethyl carbamoyl]-1H-pyrrol-3-yl}-5-methylpyrimidin-2-ylamino)-(S)-butyl ester (I-25)

In a flask containing 4-[2-(1-hydroxymethyl-(S)-propylamino)-5-methyl-pyrimidin-4-yl]-1H-pyrrole-2-carboxylic acid [1-(3-chloro-(S)-phenyl)-2-hydroxy-ethyl]-amide (1.50 g, 3.39 mmol), was added Boc-Ile-OH (1.88 g, 8.14 mmol, 2.4 equivalents) in 20 mL of dichloromethane and diisopropylethylamine (1.8 mL, 10.2 mmol, 3.0 equivalents). After stirring for 10 minutes, PyBOP (4.4 g, 8.5 mmol, 2.5 equivalents) is then added. After stirring at room temperature for 24 hours the solution was dissolved in dichloromethane and then washed with hydrochloric acid (1N) twice, sodium bicarbonate and brine. The organic layer was dried over sodium sulfate and the crude product was purified by chromatography on silica (gradient of ethyl acetate 25-70% in hexane) to afford the Boc-protected compound as a yellow solid (1.84 g), HPLC, $R_t$=8.5 min. The Boc groups were removed with HCl (4N) in dioxane diluted in acetonitrile. After 1 hour of stirring at room temperature, the solvent was evaporated under vacuum to afford the title compound (1.43 g) as the 3.HCl present. HPLC, $R_t$=4.4 min, ES+=670.1, ES-=668.2 and $^1$H NMR (MeOH-d$_4$): 9.0 (s, 1H), 8.1 (bs, 1H), 7.95 (s, 1H), 7.85 (s, 1H), 7.5 (s, 1H), 7.3-7.45 (m, 3H), 5.5 (m, 1H), 4.5-4.8 (m, 4H), 4.4 (m, 1H), 4.05 (d, 2H), 3.5-3.8 (m, 2H), 2.5 (s, 3H), 1.7-1.8 (m, 4), 1.4 (m, 2H), 1.2 (m, 2H)), 0.8-1.1 (m, 16H).

Example 5

2-(S)-Amino-3-methyl-butyric acid 2-(4-{5-[2-(2-(S)-amino-3-methyl-butyryloxy)-1-(3-chloro-(S)-phenyl)-ethylcarbamoyl]-1H-pyrrol-3-yl}-5-methyl-pyrimidin-2-ylamino)-(S)-butyl ester (I-10)

In a flask containing Boc-Val-OH (14.7 g, 67.8 mmol, 3.0 equivalents), DMAP (8.3 g, 67.8 mmol, 3.0 equivalents), and HOBt (915 mg, 6.8 mmol, 0.3 equivlanet) in 200 mL of dichloromethane was added EDCI (13.0 g, 67.8 mmol, 3.0 equivalents). After 5 minutes of stirring at room temperature, (4-[2-(1-hydroxymethyl-(S)-propylamino)-5-methyl-pyrimidin-4-yl]-1H-pyrrole-2-carboxylic acid [1-(3-chloro-(S)-phenyl)-2-hydroxy-ethyl]-amide (10.0 g, 22.6 mmol, 1.0 equivalent) was added slowly. The reaction was completed after 1 hour. The reaction mixture was dissolved in dichloromethane and washed with hydrochloric acid (1N), water, sodium bicarbonate and brine and the organic layer dried over sodium sulfate. The crude material was purified by chromatography on silica (gradient of ethyl acetate 10-100% in hexane) to afford the Boc-protected compound as a yellow solid (12.6 g), HPLC, $R_t$=7.9 min. The Boc groups were removed with HCl (2N) in ether diluted in 100 mL of acetonitrile. After 1 hour of stirring at room temperature, the solvent was evaporated under vacuum to afford the title compound (10.58 g) as the 3.HCl salt. C: 51.40%, H, 6.49%, N: 12.97%, Cl: 18.88%; calculated: C: 51.14%; H: 6.30%; N: 13.05%; Cl: 18.87%. HPLC, Rt=4.2 min, ES+=642.1, ES-=640.3 and $^1$H NMR (MeOH-d$_4$): 9.0 (s, 1H), 8.1 (bs, 1H), 7.95 (s, 1H), 7.85 (s, 1H), 7.5 (s, 1H), 7.3-7.45 (m, 3H), 5.5 (m, 1H), 4.5-4.8 (m, 4H), 4.4 (m, 1H), 4.0 (d, 2H), 2.5 (s, 3H), 2.2 (m, 2H), 1.8 (m, 2H), 0.9-1.1 (m, 15H).

Example 6

Pyrrolidine-2-(S)-carboxylic acid 2-(4-{5-[2-(pyrrolidine-2-carbamoyl)-1-(3-chloro-(S)-phenyl) ethylcarbamoyl]-1H-pyrrol-3-yl}-5-methyl-pyrimidin-2-ylamino)-(S)-butyl ester (I-28)

In a flask containing Boc-Pro-OH (2.18 g, 10.2 mmol, 3.0 equivalents), DMAP (1.24 g, 10.2 mmol, 3.0 equivalents), and HOBt (137 mg, 1.0 mmol, 0.3 equivalent) in 20 mL of dichloromethane was added EDCI (1.95 g, 10.2 mmol, 3.0 equivalents). After 5 minutes of stirring at room temperature, (4-[2-(1-hydroxymethyl-(S)-propylamino)-5-methyl-pyrimidin-4-yl]-1H-pyrrole-2-carboxylic acid [1-(3-chloro-(S)-phenyl)-2-hydroxy-ethyl]-amide (1.5 g, 3.39 mmol, 1.0 equivalent) was added slowly. After 2 hours, the reaction mixture was dissolved in dichloromethane and washed with hydrochloric acid (1N), water, sodium bicarbonate and brine. The organic layer was then dried over sodium sulfate and the crude material purified by chromatography on silica (gradient of ethyl acetate 10-80% in hexane) to afford the Boc protected compound as a yellow solid. The Boc groups were removed with HCl (2N) in ether diluted in 10 mL of acetonitrile. After 1 hour of stirring at room temperature, the solvent was evaporated under vacuum to afford the title compound (1.62 g) as the 3.HCl salt. HPLC, $R_t$=4.0 min, ES+=638.0, ES-=636.1 and $^1$H NMR (MeOH-d$_4$): 8.1 (bs, 1H), 7.95 (s, 1H), 7.9 (s, 1H), 7.3-7.6 (m, 4H), 5.5 (m, 1H), 4.5-4.75 (m, 7H), 3.4 (m, 4H), 2.5 (s, 3H), 2.3 (m, 2H), 2.1 (m, 6H), 1.8 (m, 2H), 1.1 (t, 3H).

Example 7

Other compounds of the present invention were prepared by methods substantially similar to those described in the above Examples 1-6 and those known in the art. The characterization data for these compounds is summarized in Table 2 below and includes Mass Spectral data, HPLC retention time ($R_t$), and $^1$H NMR data. Compound numbers in Table 2 correspond to the compound numbers listed in Table 1.

TABLE 2

Characterization Data for Selected Compounds of Formula I

| Compound 1 | M + 1 (obs) | M − 1 (obs) | $R_t$ | $^1$H NMR |
|---|---|---|---|---|
| I.1 | 528.00 | 526.00 | 2.7 | MeOH-d$_4$: 8.05 (s, 1H); 7.6 (s, 2H); 7.47 (s, 2H); 7.28-7.4 (m, 3H),5.4 (t, 1H); 4.35-4.48 (m, 2H); 4.18-4.35(m, 3H); 2.38 (s, 3H),2.07 (s, 3H); 1.98 (s, 3H); 1.56-1.80 (m, 2H); 1.02 (t, 3H) |

TABLE 2-continued

Characterization Data for Selected Compounds of Formula I

| Compound 1 | M + 1 (obs) | M − 1 (obs) | $R_t$ | $^1$H NMR |
|---|---|---|---|---|
| I-2 | 486.2 | 484.1 | | MeOH-$d_4$: 8.05(s, 1H), 7.92 (s, 1H), 7.8 (s, 1H), 7.45 (s, 1H), 7.25-7.36,(m, 3H), 5.16 (t, 1H), 4.30-4.35((m, 1H), 4.20-4.25(m, 1H), 3.82-3.9 (m, 2H), 2.46(s, 3H), 1.95(s, 3H), 1.65-1.85(m, 2H),1.06 (t, 3H) |
| I-3 | 516.00 | 514.00 | 2.5 | MeOH-$d_4$: 7.98 (s, 1H), 7.6 (m, 2H); 7.42 (s, 1H); 7.22-7.35 (m,3H),5.14 (t, IH); 4.0-4.35 (m, 5H), 3.84 (d, 2H); 2.35 (s, 3H), ,1.52-1.74 (m., 2H); 1.18 (t, 3H), 0.98 (t, 3H) |
| I-4 | 584.2 | 582.2 | 3.07 | — |
| I-5 | 588 | 586 | 3.05 | MeOH-$d_4$: 8.86 (d, 1H), 8-8.08 (m, 2H); 7.97 (s, 1H); 7.78 (s, 1H); 7.48 9s, 1H); 7.3-7.4,(m, 3H); 5.42 (t, 1H); 4.3 8-4.48 (m, 4H); 3.95-4.20 (m, 6H); 1.6-1.82 (m, 2H); 1.22 (t, 3H); 1.13 (t, 3H); 1.07 (t, 3H) |
| I-6 | 660 | 658 | 3.91 | MeOH-$d_4$: 8.15 (s, 1H); 8.10 (s, 1H); 7.50 (s, 1H); 7.30-7.40,(m, 4H); 5.38 (t, 1H); 4.32448 (m, 6H); 4.0-4.2 (m, 5H); ,2.46 (s, 3H); 1.6-1.82 (m, 2H); 1.27 (t, 6H); 1.18 (t, 3H); ,1.05 (t, 3H) |
| I-7 | 715.9 | 714.2 | — | MeOH-$d_4$: 7.2-8.1 (m, 7H), 5.4 (m, 1H), 4.0-4.4 (m,13), 2.4 (s, 3H), 1.6-1.8 (2x m, 2H), 1.2 (m, 12), 1.1 (t, 3H). |
| I-8 | 616 | 614 | 3.3 | MeOH-$d_4$: 8.0 (s, 1H); 7.78 (s, 1H); 7.7 (s, 1H); 7.47 (s, 1H); ,7.27-7.38 (m, 2H); 5.4S (t, 1H); 4.68-4.83 (m, 2H); 4.27-4.46,(ni, 4H); 4.10-4.18 (m, 1H); 2.40 (s, 3H); 1.58-1.78 (m, 2H); ,1.08-1.26 (m, 12H); 1.02 (t, 3H) |
| I-9 | 530 | 528 | 2.6 | MeOH-$d_4$: 7.98 (s, 1H); 7.87 (s, 1H); 7.76 (s, 1H); 7.38 (s, 1H); ,7.20-7.34 (m, 3H); 5.12 (t, 1H), 4.66-4.75 (m, 1H); 4.28-4.38,(m, 1H); 4.12-4.20 (m, 1H); 3.80-3.88 (m, 2H); 2.47 (s, 3H); 1.58-1.82 (m, 2H); |
| I-10 | 642.0 | 640 | 1.80 | MeOH-$d_4$: 8.08 (br. 1H); 7.94 (s, 1H); 7.73 (s, 1H); 7.48 (s, 1H); 7.30-7.42 (m, 3H); ,5.48-5.58 (m, 1H); 4.50-4.68 (m, 3H); 4.43 (s, 2H), 3.96 (dd, 2H),2.47 (s, 3H); 2.12-2.28 (m, 2H); 1.74-1.86 (m, 2H); 0.88-1.06 (m, iSH), |
| I-11 | — | — | 3.7 | MeOH-$d_4$: 8.0 (s, 1H), 7.3-7.6 (m, 6H), 5.45 (m, 1H),4.3-4.45 (m, 3H), 4.1-4.25 (m, 2H). 2.3 (s, 3H), 2.55-2.75 (2x m, 2H)., 1.1 (s, 9H), 1.06 (s, 9H), 1.0 (t, 3H). |
| I-12 | 514 | 512 | 2.7 | MeOH-$d_4$: 8.65 (br. 1H); 8.02 (s, 1H); 7.8 (s, 1H); 7.78 (s, 1H); 7.43 (s, 1H); ,7.22-7.37 (m, 3H); 5.16 (t, 1H); 4.16-4.35 (m, 2H); 3.8-3.88,(m, 2H); 2.44-2.54 (m, 1H); 2.46 (s, 3H); 1.61-1.84 (m, 2H); ,0.98-1.07 (m, 9H) |
| I-13 | 580.0 | 578.0 | 2.58 | MeOH-$d_4$: 8.0 (s, 1H); 7.92 (s, 2H); 7.45 (s, 1H); 7.23-7.38 (m, 3H); 5.15 (t, 1H); 4.47 (br, 1H); 4.12-4.32 (m, 2H),4.04-4.12 (m, 4H); 3.86 (d, 2H); 2.45 (s, 3H); 1.80-1.90 (m, 1H); 1.62-1.72 (m, 1H); 1.24 (t, 6H); 1.05 (t, 3H) |
| I-14 | 530 | 528 | 2.7 | MeOH-$d_4$: 8.0 (s, 1H); 7.9 (s, 1H); 7.77 (s, 1H); 7.48 (s, 1H); 7.28-7.40 ,(m, 3H); 5.45 (t, 1H); 4.78-4.85 (m, 1H); 4.38-4.48 (m, 3H); 3.6-4.75,(m, 4H); 22.47 (s, 3H); 1.57-1.85 (m, 2H); 1.18-1.27 (m, 6H); 1.05 (t, 3H); |
| I-15 | 560 | 558 | 2.4 | MeOH-$d_4$: 8.02 (s, 1H); 7.92 (s, 1H); 7.78 (s, 1H); 7.45 (s, 1H); 7.3-7.48 (m, 2H); 7.25-7.28 (m, 1H); 5.14 (t, 1H); 4.40-4.50 (m, 1H); 4.18-4.26 (ni, 1H),3.98-4.1 (m, 2H); 3.84 (d, 2H); 3.46-3.56 (m, 2H); 3.38-3.47 (m, 2H); 3.28 (s, 3H); 2.48 (s, 3H); 1.60-1.87 (m, 2H); 1.06 (t, 3H) |

TABLE 2-continued

Characterization Data for Selected Compounds of Formula I

| Compound 1 | M + 1 (obs) | M − 1 (obs) | $R_t$ | $^1$H NMR |
|---|---|---|---|---|
| I-16 | 604 | 602 | 2.2 | MeOH-$d_4$: 8.55-8.62 (d, 1H); 8.02 (s, 1H); 7.93 (s, 1H); 7.78 (s, 1H);,7.43 (s, 1H); 7.22-7.38 (m, 3H); 5.10-5.16 (m, 1H); 4.4-4.5 (m, 1H); ,3.92-4.10 (m, 3H); 3.80-3.88 (d, 2H); 3.4-3.54 (m, 4H); 2.47 (s, 3H); ,1.6-1.85 (m, 2H); 1.08 (t, 3H) |
| I-17 | — | — | 2.8 | MeOH-$d_4$: 8.6 (s, 1H), 7.9-8.05 (2x s, 2H), ,7.75 (m, 1H), 7.2-7.4 (m, 4H), 5.15 (m, 1H), 4.1-4.3 (2x m, 2H),3.8 (m, 2H), 2.4 (s, 3H), 1.6-1.8 (2x m, 2H), 1.05 (s, 9H). |
| I-18 | — | — | 2.46 | MeOH-$d_4$: 8.0 (s, 1H), 7.8, (s, 1H), 7.95(s, 1H), 7.5 (s, 1H), 7.3-7.4 (m, 4H), 5.4 (m, 1H) 4.5 (m, 1H), 4.3-4.4 (m, 2H),4.25 (m, 1H), 2.6 (m/s/s overlapped, 8H), 1.8 (m, IH),1.7 (m, 1H), 1.05 (t, 3H) |
| I-19 | 670.1 | — | 2 | MeOH-$d_4$8.0 (br. 1H); 7.47-7.68 (m, 3H); 7.3-7.48 (m, 3H); 5.5 (br, 1H); 4.52 (br. 2H),4.32 (m, 3H); 3.3-3.4 (m, 4H); 2.35 (s, 3H); 1.6-1.8 (m, 2H); 1.0 (m, 21H) |
| I-20 | 670.1 | — | 1.84 | MeOH-$d_4$7.85-8.2 (m, 3H); 7.3-7.6 (m, 4H); 5.6 (s, 1H); 5.7 (m, 2H); 4.4-4.6 (m, 2H); 3.95-4.05 (m, 2H);,2.7 (s, 6H); 2.5 (s, 3H); 2.3 (br. 2H); 1.8 (br. 2H); 0.9-1.1 (m, 15H), |
| I-21 | 676.0 | 674.0 | 2.6 | MeOH-$d_4$: 8.05 (s, 1H); 7.62 (s, 2H); 7.49 (s, 1H); 7.3-7.42 (m, 3H),5.45 (t, 1H); 7.47-7.58 (m, 2H); 4.3-4.4 (m, 2H); 4.2-4.28 (m, 1H),4.18 (s, 3H); 4.05 (m, 2H); 3.6 (m, 2H); 3.55 (m, 2H); 3.4-3.5 9m, 4H); 2.38 (s, 3H); 1.52-1.74 (m, 2H); 1.05 (t, 3H) |
| I-22 | 586 | | 1.7 | MeOH-$d_4$: 8.1 (s, 1H); 7.9 (s, 1H); 7.77 (s, 1H); 7.5 (s, 1H); 7.3-7.42 (m, 3H),5.52 (t, 1H); 4.6-4.7 (m, 2H); 4.44-4.6 (m, 2H); 4.1-4.2 (m, 2H); 2.47 ,(s, 3H); 2.8 (m, 2H); 1.5 (d, 3H); 1.45 (d, 3H); 1.02 (t, 3H) |
| I-23 | 603.9 | 601.9 | 2.42 | (DMSO-$D_6$) 0.9 (t, 3H), 1.5 (m, 1H), 1.8 (m, 1H), 2.3 (s, 3H), 3.75 (bm, 1H), 4.1 (overlap two m, 4H), 5.25 (m, 1H), 6.8 (bs, 1H), 7.4 (m, 4H), 7.5 (apparent bd, 2H), 7.8 (bs, 1H), 8.1 (s, 1H), 9.0 (bs, 1H),, |

Example 8

As described herein, the present compounds are useful as prodrugs and, accordingly, impart improved physical and/or physiological characteristics over the parent compound. Such characteristics include half-life and water solubility. In certain embodiments, a compound of the present invention provides improvement with regard to one or more physical or physiological characteristics. In other embodiments, a compound of the present invention imparts improvement with regard to one or more physical and physiological characteristics. A summary of the results of comparison between certain compounds of the present invention and the parent compound is set forth in Table 3 below wherein all pharmacokinetic data reported was obtained in rat.

As used herein, the phrase "Relative AUC" refers to the ration of the area under the curve for a compound of the present invention and the area under the curve for the parent compound. Unless otherwise indicated, the data was obtained for the designated compound as the free base. The term "T½ (hr)" refers to the half life of the compound in hours. As used in Table 3, the term "Solubility" relates to the water solubility of the designated compound in mg per mL at the designated pH. Compound numbers in Table 3 correspond to the compound numbers listed in Table 1.

TABLE 3

Physical and Physiological Data for Representative Compounds

| Compound | Relative AUC | T1/2 (hr) | Solubility/pH |
|---|---|---|---|
| Parent | 1 | 2 | 4.7/1 |
| | | | 0.015/7 |
| I-1 | 1.1 | 7.6 | — |
| I-1 (HCl salt) | 2.02 | 4.54 | 18.98/2.2 |
| I-2 | 0.6 | 4.15 | — |
| I-3 | 0.2 | 12 | — |
| I-4 | 0.74 | 7.6 | — |
| I-5 | 0.53 | 6.7 | — |
| I-10 | 5 | 2.2 | 11.5/3.3 |
| I-11 | 1.2 | 6.2 | — |
| I-13 | 0.07 | NA | — |
| I-18 | — | — | 12.6/6.87 |

TABLE 3-continued

Physical and Physiological Data for Representative Compounds

| Compound | Relative AUC | T1/2 (hr) | Solubility/pH |
|---|---|---|---|
| I-20 (HCl salt) | 4.35 | 5.8 | 7.71/3.8 |
| I-21 Ms salt | 1.23 | 3.2 | 12.4/2.5 |
| I-22 (HCl salt) | 0.33 | 4.6 | — |
| I-23 (Na salt) | 0.26 | 2.95 | 3.8/7.15 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound selected from the group consisting of:

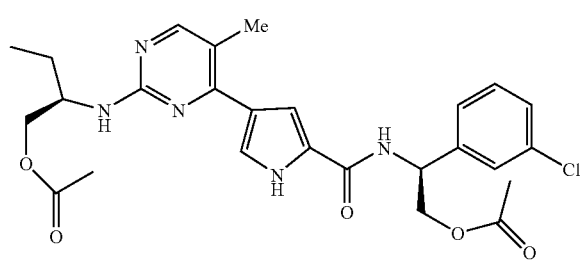

I-1

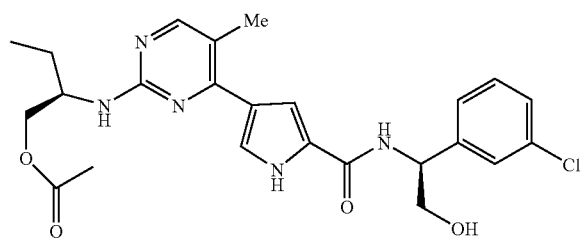

I-2

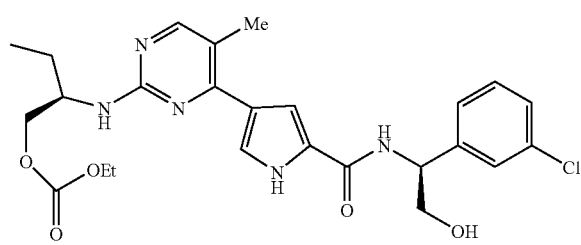

I-3

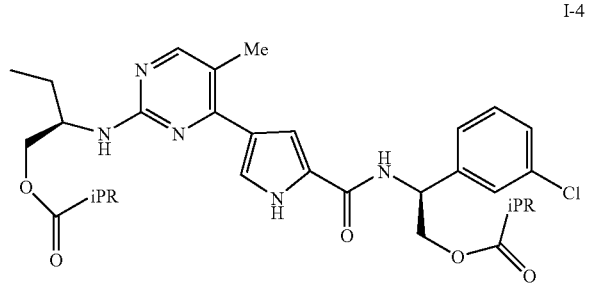

I-4

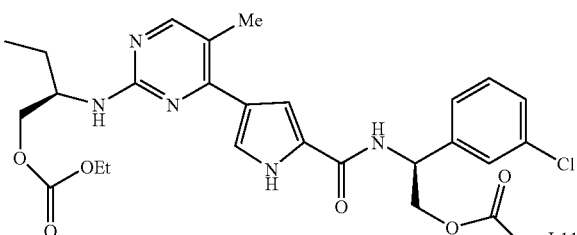

I-5

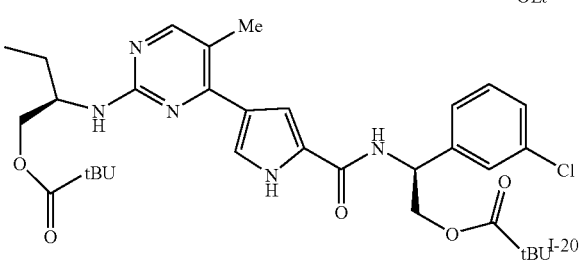

I-11

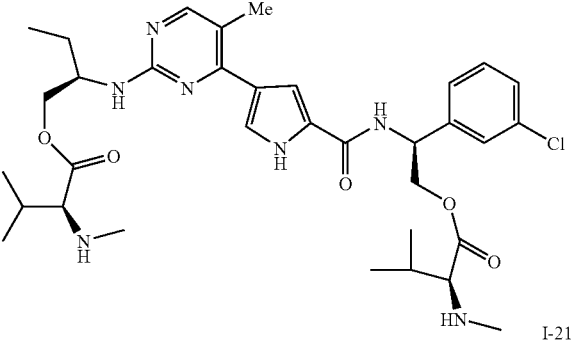

I-20

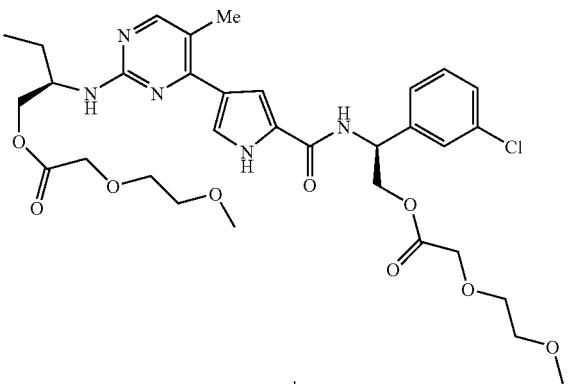

I-21

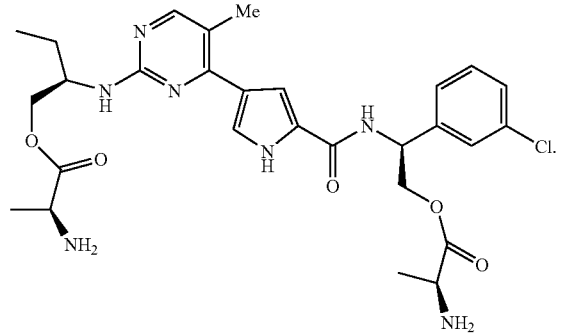

and

I-22

2. A composition comprising a compound according to claim 1, and a pharmaceutically acceptable adjuvant, vehicle, or carrier.

3. The composition according to claim 2, wherein said composition further comprises an additional therapeutic agent selected from a chemotherapeutic or anti-proliferative agent, wherein said anti-proliferative agent is mechlorethamine, chlorambucil, cyclophosphamide, melphalan, ifosfamide, methotrexate, 6-mercaptopurine, 5-fluorouracil, cytarabile, gemcitabine, vinblastine, vincristine, vinorelbine, paclitaxel, etoposide, irinotecan, topotecan, doxorubicin, bleomycin, mitomycin, carmustine, lomustine, cisplatin, carboplatin, tamoxifen, leuprolide, flutamide, and megestrol, imatinib, adriamycin, dexamethasone, or cyclophosphamide; an anti-inflammatory agent, wherein said anti-inflammatory agent is albuterol or Singulair®; an agent for treating Alzheimer's disease selected from Aricept® and Excelon®; or an agent for treating cardiovascular disease, wherein said agent is a beta-blocker, an ACE inhibitor, a diuretic, a nitrate, a calcium channel blocker, or a statin.

4. A method of treating or lessening the severity of a disease, condition or disorder, in a patient in need thereof, wherein said disease or disorder is: a cancer selected from breast cancer, colon cancer, kidney carcinoma, lung cancer, melanoma, ovarian cancer, pancreatic cancer, or prostate cancer; a cardiovascular disorder, wherein said cardiovascular disorder is selected from restenosis, stroke, atherosclerosis, or cardiomegaly; Alzheimer's disease; or asthma, comprising the step of administering to said patient:
   a) a composition according to claim 2; or
   b) a compound according to claim 1.

5. The method according to claim 4, wherein said disease, disorder, or condition is a cancer selected from breast cancer, colon cancer, kidney carcinoma, lung cancer, melanoma, ovarian cancer, pancreatic cancer, or prostate cancer.

6. The method according to claim 5, wherein said disease, disorder, or condition is melanoma or a cancer selected from breast cancer, colon cancer, or pancreatic cancer.

* * * * *